United States Patent [19]

Selner et al.

[11] 4,392,487

[45] Jul. 12, 1983

[54] METHOD AND APPARATUS FOR FOOT STABILIZATION

[76] Inventors: Allen J. Selner; Marc D. Selner, both of 13320 Riverside Dr. #216, both of Sherman Oaks, Calif. 91423

[21] Appl. No.: 180,811

[22] Filed: Aug. 25, 1980

[51] Int. Cl.³ .................................................. A61F 3/00
[52] U.S. Cl. .................................. 128/80 H; 128/166
[58] Field of Search ...................... 128/166.5, 166, 157, 128/80 H

[56] References Cited

U.S. PATENT DOCUMENTS

| | | | |
|---|---|---|---|
| 1,156,621 | 10/1915 | O'Dwyer | 128/166.5 |
| 1,283,335 | 10/1918 | Shillcock | |
| 1,365,512 | 1/1921 | Lewis | 128/166.5 |
| 1,443,844 | 1/1923 | Jensen | 128/166 |
| 1,462,534 | 7/1923 | Condylis et al. | 128/166.5 |
| 1,465,970 | 8/1923 | Cleveland et al. | 128/166.5 |
| 1,788,852 | 1/1931 | Arthur | |
| 2,292,643 | 8/1942 | Layana | 128/166.5 |
| 2,358,966 | 9/1944 | Einstoss | 128/166.5 |
| 2,708,930 | 5/1955 | Lowman | 128/80 |
| 3,383,708 | 5/1968 | Pappas | 128/166 X |
| 3,504,668 | 4/1970 | Boudon | 128/80 |
| 3,699,959 | 10/1972 | Garrahan et al. | 128/166 |
| 3,867,930 | 2/1975 | Brown | 128/83 |
| 4,084,586 | 4/1978 | Hettick | 128/157 |

Primary Examiner—John D. Yasko
Attorney, Agent, or Firm—Fulwider, Patton, Rieber, Lee & Utecht

[57] ABSTRACT

A method and apparatus for stabilizing the foot to control gait wherein an adjustable elastic sleeve and a substantially inelastic strap are wrapped around the foot in a prescribed fashion with the strap ends anchored to the sleeve so as to limit excessive pronation and assist in resupination of the foot. In one embodiment, the sleeve is wrapped around the arch of the foot and the strap extends from a location on the sleeve adjacent the bottom of the foot, up across the instep, over the top of the foot and around the heel, from which position the strap extends back to the sleeve and fastens thereto near the instep. One or more guides on the sleeve help maintain the strap in the desired position on the foot and the strap may be folded over on itself to aid in conforming to the curvature of the foot in the heel region. In another embodiment the sleeve is wrapped around the arch, but the strap extends from opposite sides of the sleeve directly around the heel. Alternatively, the sleeve can be placed around the ankle and the strap can extend from opposite sides of the sleeve below the heel to serve as an ankle and leg support.

11 Claims, 9 Drawing Figures

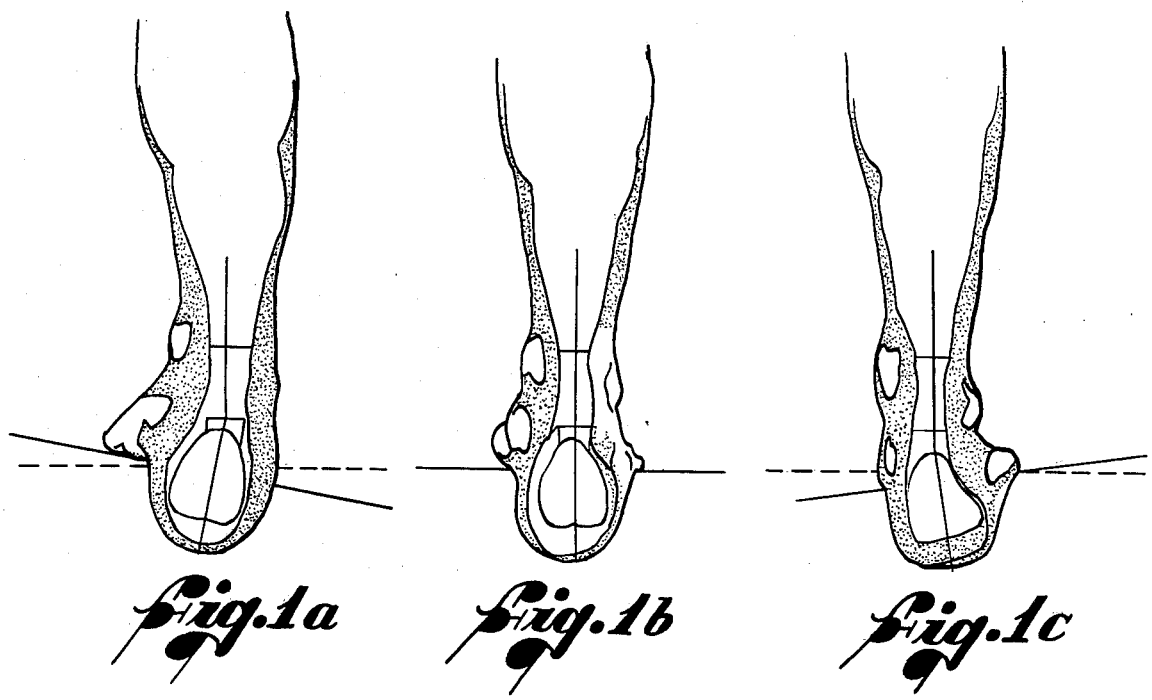
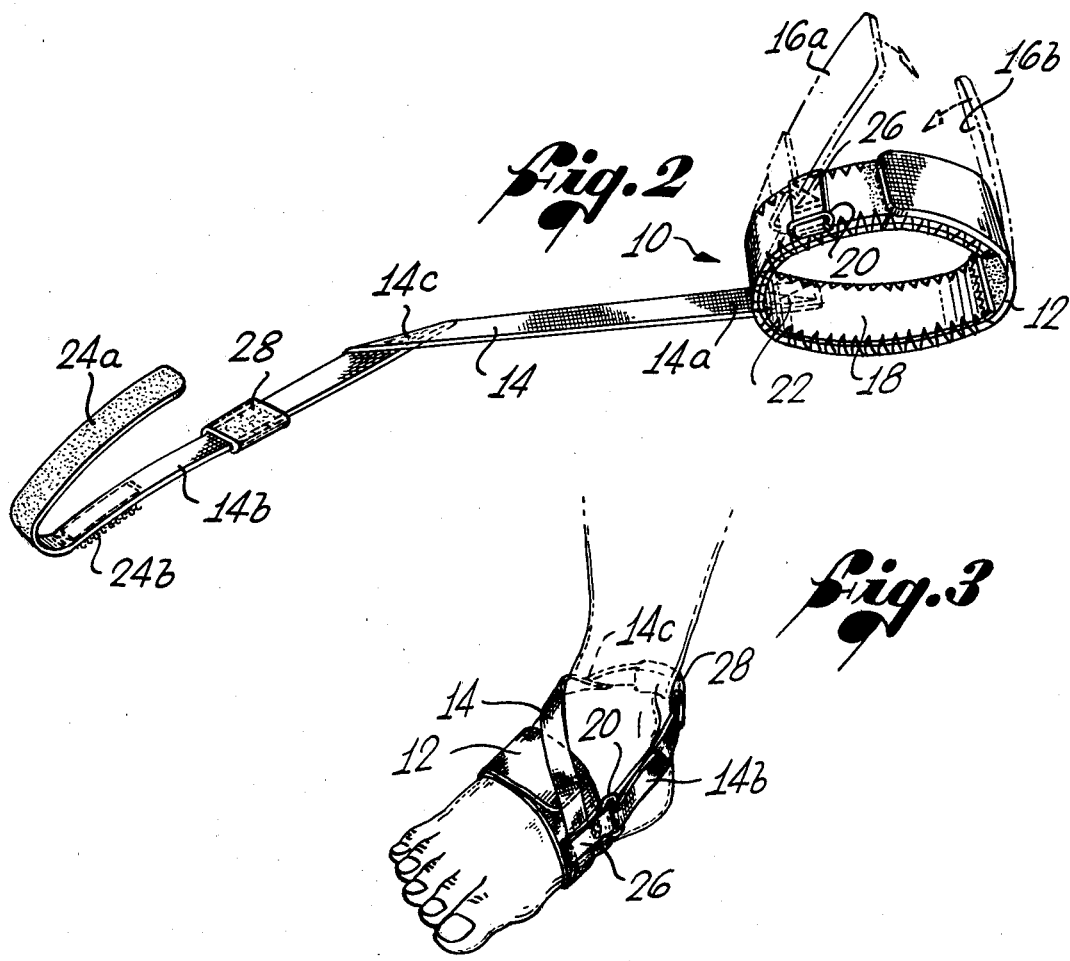

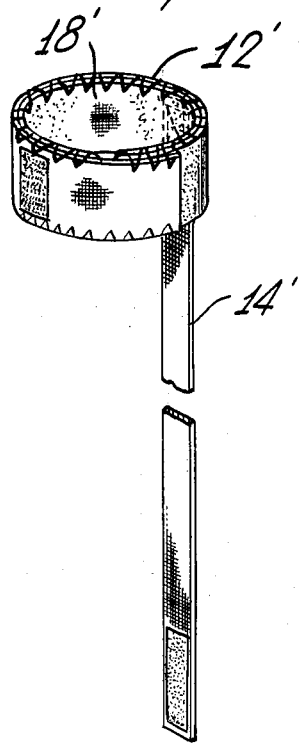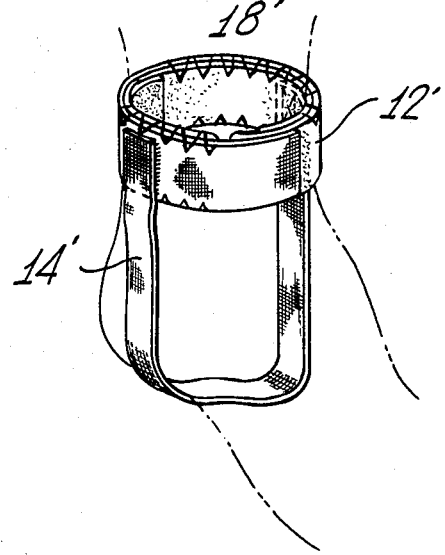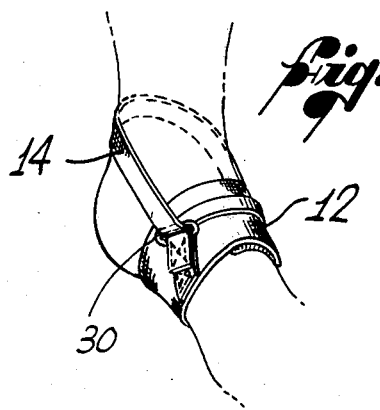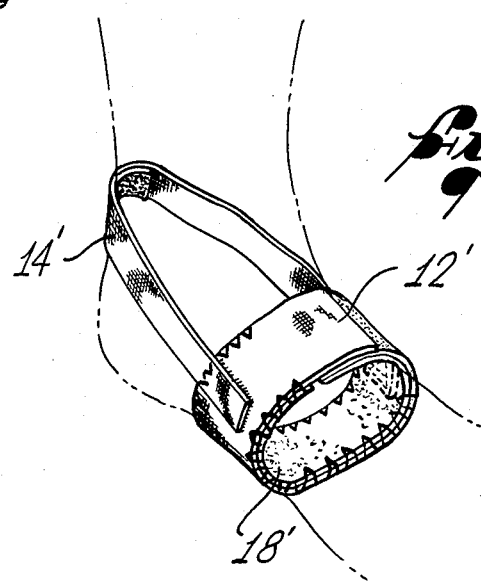

METHOD AND APPARATUS FOR FOOT STABILIZATION

BACKGROUND OF THE INVENTION

This invention relates generally to orthopedic devices for the feet, and relates more specifically to a foot stabilization device for controllling gait by limiting excessive pronation and assisting in resupination of the foot during walking or running.

Various orthopedic devices intended to support or control motion of the foot and ankle have been known for a number of years, and by way of example, several forms of such devices can be found in U.S. Pat. Nos. 1,283,335; 1,565,259; 1,788,852; 2,292,643; 2,358,966; 2,708,930; 3,504,668; 3,867,930; and 4,084,586.

A normal human gait cycle consists of three phases: the contact phase in which the heel alone initially makes contact with the ground, the mid-stance phase in which the entire sole or plantar surface of the foot is in contact with the ground, and the propulsive phase wherein the balls of the foot and the toes push off. During the gait cycle, the foot and ankle tend naturally first to undergo movement known as pronation and then to move in a manner known as supination. While these movements of the foot and ankle are complex and can only be accurately described with reference to the three conventional anatomical planes (i.e., the sagittal, frontal and transverse planes), in simple terms pronation is an inward rolling and supination is an outward rolling of the foot and ankle.

More specifically, pronation and supination of the foot and ankle are a function primarily of the subtalar joint and the midtarsal joints. The subtalar joint is defined as the articulation between the talus and calcaneus (heel) bones. The midtarsal joints comprise the calcanealcuboid joint, which is defined as the articulation of the calcaneus and cuboid bones, and the talar-navicular joint, which is defined as the articulation of the talus (ankle) and the navicular bones. The navicular bone forms part of the arch structure.

A certain amount of pronation of the foot during walking or running is desirable. Generally speaking, pronationn occurs during the contact phase and about the first half of the mid-stance phase of a normal gait cycle. In the pronated position, the bones of the foot tend to become mobile or loose relative to one another so that the plantar surface can adapt to possibly uneven terrain. During the last half of the mid-stance phase and during the propulsive phase, however, resupination is essential so that the bones of the foot become relatively stable or locked to enable one to push-off.

Although some pronation is normal, many persons are troubled by excessive pronation in which the foot and ankle roll too far inwardly and the bones of the foot become hypermobile relative to one another. The combination of excessive pronation and resupination during a gait cycle can result in exaggerated back and forth rotational movement of the leg and knee with accompanying results that are highly undesirable. For example, various forms of muscular fatigue in children (sometimes called "growing pains") and in adults (such as back pain and leg fatigue) have been traced to excessive pronation. Likewise, excessive pronation has been found to be a cause of arch strain, heel pain, pain in the knee joint and the patella (knee cap), and foot deformities such as bunions and hammer toes (which in turn can result in corns and calluses). The effects of excessive pronation are particularly a problem for athletes, including those who run or jog.

Despite the existence of the aforementioned orthopedic devices, the most commonly attempted solution to the problem of excessive pronation has been use of conventional arch support wedges. This is believed to be because pronation is accompanied by a general stretching and flattening of the arch, and persons with flattened arches tend to suffer more frequently from the effects of excessive pronation. Use of arch support wedges has been found to be a generally ineffective solution, however, because it is directed to a sympton rather than the source of the problem. Some persons have flattened arches and do not excessively pronate; other persons with raised arches suffer greatly from the effects of excessive pronation. Rather than being due to flattened arches, excessive pronation is primarily the result of the internal structure of the foot and ankle, and in particular the motions of the subtalar and midtarsal joints; it is also influenced by external forces generated by knock-kneed, pigeon-toed or duck walking, for instance. Arch support wedges cannot control these factors, particularly in a person with naturally high arches, and even feet characterized by flattened arches will tend to roll right over conventional arch support wedges. Moreover, arch support wedges require shoes and thus are impractical for certain athletes such as dancers.

Another approach to the problem has been to carefully wrap adhesive tape circularly around the arch and to connect it with tape extending rearwardly along each side of the foot and around the heel. The tape extending around the heel serves to maintain the circular portion in position and to act as a lateral restraint on foot motion thereby preventing excessive pronation. To be effective, however, the tape must be applied very carefully in a prescribed manner by a qualified professional. Thus, this solution is not adapted for ordinary self-application. Also, tape has the disadvantage of stretching after a short time and any particular taping can last at most a few days. Further, the direction of pull and pressure cannot be adjusted after wrapping. In addition, tape does not assist in resupination of the foot. Tape also is irritating and cannot be used over.

The primary objective of the present invention is a more effective method and apparatus, which is capable of self-application, for restricting excessive pronation and assisting in resupination to control gait and thereby minimize resulting problems. The present invention clearly fulfills this objective.

SUMMARY OF THE INVENTION

Briefly, and in general terms, the present invention resides in a method and apparatus for stabilizing movement of the foot to control gait wherein a sleeve and a connecting strap are wrapped around the foot in a prescribed fashion with the strap ends anchored to the sleeve. The sleeve and strap are constructed and applied to align the foot in a preferred position and to effectively restrain the foot from excessively pronating, as well as to assist in resupination of the foot during walking or running.

More specifically, in a presently preferred embodiment, the sleeve is formed of a relatively elongate sheet of material having longitudinal elasticity only and opposite ends that are adapted to be releasably joined together for adjustability. The strap is relatively narrow and elongate, and is formed of material that is substantially inelastic in the longitudinal direction. Means are provided on the ends of the strap and on the sleeve for fastening the strap ends to the sleeve. Although the sleeve is elastic so as not to overly restrict movement of bones within the foot, it is also important that the sleeve be locked in position on the foot so that the strap can exert appropriate resistive forces against excessive pronation, and to this end the interior side of the sleeve is lined with a gripping material.

In accordance with a presently preferred method of the invention, the sleeve is wrapped snuggly around the arch of the foot with the ends of the sleeve joined together. The strap extends from a location on the sleeve adjacent the bottom of the foot, up across the instep, over the top of the foot and around the heel, from which position the strap extends back to the sleeve and fastens thereto near the instep. The strap is then tightened with the foot aligned in a preferred position (turned inwardly and rolled slightly outward). The substantial inelasticity of the strap and the fact that sleeve is locked around the foot with both ends of the strap anchored to the sleeve on the medial side of the foot, all contribute to restraining the foot from excessive pronation and assisting in resupination during walking or running.

Preferably, one or more guides for the strap are provided on the sleeve to maintain the strap in optimum position around the foot. The strap may be folded over on itself to aid in conforming to the curvature of the foot around the heel. For comfort, a heel pad may be supplied on the strap.

In an alternative embodiment of the invention, a similar sleeve has the ends of a strap attached to it on opposite sides of the foot. Again, the strap is substantially inelastic in the longitudinal direction. The strap is tightened with the foot aligned in a turned inward position so that the device likewise acts to restrain excessive pronation. This alternative embodiment can also be used as an ankle and leg support by placing the sleeve around the leg and positioning the strap below the heel.

Other aspects and advantages of the invention will become apparent from the following detailed description taken in conjunction with the accompanying drawings.

BRIEF DESCRIPTION OF THE DRAWINGS

The accompanying drawings illustrate various embodiments of the method and apparatus of the invention, in which:

FIG. 1 a–c are fragmented anatomical illustrations in the frontal plane taken from the back of the foot showing the supinated, neutral, and pronated positions, respectively;

FIG. 2 is a perspective view of a presently preferred embodiment of the foot stabilization apparatus shown in an unassembled condition;

FIG. 3 is a perspective view of the assembled foot stabilization apparatus of FIG. 2 taken from the front of the foot;

FIG. 4 is a perspective view of another embodiment of the invention in a partly unassembled condition;

FIG. 5 is a perspective of the assembled apparatus shown in FIG. 4 taken from the front of the foot and ankle;

FIG. 6 is a perspective view taken from the front of the foot showing the apparatus of FIG. 4 assembled in an alternative manner; and FIG. 7 is a perspective view taken from the front of the foot showing a modified version of the apparatus of FIGS. 2 and 3 assembled on the foot.

DETAILED DESCRIPTION

As shown in the drawings for purposes of illustration, and particularly in FIGS. 2 and 3 thereof, the present invention is embodied in a foot stabilization device indicated generally by reference numeral 10, of which the principal components are a sleeve 12 and a strap 14 whose opposite ends fasten to the sleeve, and in a method of applying the device to the foot for effectively resisting excessive pronation and assisting in resupination of the foot. The sleeve 12 is formed by an elongate and generally rectangular sheet of material which is elastic in the longitudinal or circumferential direction only. In contrast the strap 14, which is relatively narrow and long, is substantially inelastic.

The opposite ends of the material forming the sleeve 12 are provided with mating portions of thistle cloth fastening material 16a, b, such as VELCRO brand material, which can be fastened to one another. By this means, the sleeve can be opened up for ease of wrapping it around the arch of the foot (shown in phantom in FIG. 2). Also, the fastening material 16a, b overlap sufficiently so that the sleeve 12 can be adjusted to accommodate various size feet.

Secured to the interior surface of the sleeve 12 is a strip 18 of elastic gripping material of well known construction which extends almost completely around the sleeve. The remaining inside of the sleeve is the same material as the outside elastic material. The strip 18 of gripping material serves to anchor the sleeve to the foot to provide a base from which the strap 14 can be pulled tight (FIG. 3). An attachment loop 20 is provided on the sleeve at a location that will be between the medial side center line and the bottom of the foot on the medial side (i.e., the medial plantar location) when the sleeve is wrapped around the arch of the foot.

The strap 14 has one end 14a secured by stitching or other means to the sleeve 12 at a location 22 which will be at the lateral side approximately at the bottom of the foot (i.e. lateral plantar location) when the sleeve is wrapped around the arch of the foot. As illustrated, this strap end 14a extends below the foot at an angle which directs the strap rearwardly underneath the foot. The other end 14b of the strap 14 carries opposite Velcro portions 24a, b which attach to each other after the strap is placed around the foot, threaded through the loop 20, tightened, and folded back onto itself. It will become apparent that this connection of strap end 14b gives a better mechanical advantage to resist excessive pronation than if the end were connected higher up on the medial side of the sleeve.

With reference to dimension, the strap 14 can be ½ to 1 inch in width and the sleeve can be 2 to 4 inches wide. A nylon mesh is suitable for the sleeve, with the gripping material formed of neoprene. The strap can be formed of an inelastic nylon weave. Normally in this embodiment the sleeve is located in the area behind the big toe joints to the mid part of the arch.

As shown in FIG. 3, after the sleeve 12 has been positioned around the arch, the strap 14 is wrapped obliquely across the bottom of the foot, obliquely up and over the arch, around the ankle and then back along the medial side of the foot in order to connect end 14b to attachment loop 20. Since the strip 18 of gripping material grips the foot and prevents the sleeve 12 from moving, the strap 14 is anchored and can be pulled tightly around the heel.

With reference now to FIG. 1 of the drawings, the manner in which the foot stabilization device 10 of the invention functions to resist excessive pronation and to assist in resupination of the foot will be described. FIG. 1a–c consists of three anatomical illustrations showing the foot in the supinated, neutral and pronated positions, respectively.

As mentioned above, pronation and supination can be accurately described only in the three conventional anatomical planes (the sagittal, frontal and transverse planes), primarily with reference to the subtalar joint. By way of background, pivotal movement of the foot in the sagittal plane is termed dorsi flexion (upward movement of the front of the foot) or plantar flexion (downward movement). In the frontal plane, eversion is a pivotal movement of the bottom of the foot away from the midline of the body, while inversion is movement towards the midline. Finally, in the transverse plane abduction is defined as a pivotal movement of the front of the foot away from the midline of the body and adduction is movement toward the midline.

The foot is normally in the pronated position upon heel contact with the ground and continuing through about the first half of the mid-stance phase of a gait cycle. In the pronated position the foot tends to be abducted, everted and dorsi flexed. In other words, the front of the foot is flexed upwardly and turned outwardly, while the bottom of the foot is rolled away from the midline of the body. During the last half of the mid-stance phase and as contact comes up to the toes for push-off, the foot is normally supinated, i.e., the front of the foot is flexed downwardly and turned inwardly, with the bottom of the foot rolled toward the midline.

To prevent excessive pronation, the foot is held in a position of slight inward turn and outward roll as the strap 14 is pulled tightly around the foot and fastened through the attachment loop 20. Then, while walking or running, as the heel contacts the ground the strap 14 exerts resistive forces tending to prevent the foot from excessively pronating. That is, the strap restrains the arch region of the foot relative to the heel so that the front of the foot does not excessively flex upwardly or turn outwardly, and so that the bottom of the foot does not excessively roll away from the midline of the body. The points at which the strap ends 14a, b attach to the sleeve 12 are especially suited to this purpose. It is also important in this regard that the sleeve 12 is substantially inelastic in the lateral direction (i.e., the direction of pull by the strap).

More specifically, the portion of the strap 14 extending between the lateral plantar connection 22 on the sleeve 12 and the ankle tends to support the arch joints from coming down and pulls up to prevent the foot from collapsing. The portion of the strap 14 extending from the ankle to the medial side connection resists the front part of the foot from turning outwardly. During pronation, the strap 14 first pulls up on the arch to resist lengthening and spreading of the foot and then pulls on the foot to resist outward turning. When the foot hits the ground, the sleeve 12 will resist foot spreading, while stretching somewhat, and as foot contact progresses to the toes and the foot is lifted off the ground the sleeve will return to its original shape and place the foot in proper starting condition.

The combined actions of the sleeve and strap throughout the phases of the gait cycle, as thus described, serve to control foot motions relative to the subtalar joint. As a result, problems associated with excessive pronation are greatly diminished.

Referring again to FIGS. 2 and 3, a guide 26 is provided on the medial side of the sleeve 12 through which the strap 14 extends. The guide 26 is formed by a piece of material that is fastened to the sleeve by longitudinal or circumferential stitching spaced far enough apart to receive the strap between the material and the sleeve. Advantageously, the guide 26 is located forwardly of the attachment loop 20 and the guide material extends through the loop, doubles back on itself and is stitched to anchor the loop to the sleeve. The guide 26 serves to hold the strap 14 in the desired position on the foot as it passes over the foot above the arch.

To conform more closely to the natural curvature of the foot near the heel, the strap 14 is folded over on itself at an oblique angle and stitched together at a location 14c about midway along its length. When applied to the foot, this fold is intended to fall just under the lateral malleolus (the distal end of the tibia which forms the well-known prominence on the lateral side of the ankle). The resulting shape of the strap 14 also keeps it low on the heel and tends to prevent it from riding up on the achilles tendon.

An optional heel pad 28 on the strap may be included for additional comfort.

Instead of folding the strap 14 over on itself, a second guide 30 may be provided as shown in FIG. 7. This second guide 30 is a loop similar to the attachment loop 20, but is fastened on the sleeve 12 at a location placing it on the lateral side of the foot, approximately opposite the attachment loop. Also like the attachment loop 20, the second guide is secured to the sleeve by a piece of material which is inserted through the guide, doubled back on itself and stitched to the sleeve. The second guide 30 is disposed at an angle to the sleeve 12 such that the strap 14 can be wrapped across the top of the foot generally parallel to the sleeve, folded over as it passes through the guide and redirected toward the heel. In this way the second guide 30 serves to hold the strap 14 in the desired position on the foot. The remainder of the foot stabilization device shown in FIG. 7 is identical to the device shown in FIGS. 2 and 3, except that a heel pad is not shown.

An alternative embodiment of the foot stabilization device is shown in FIG. 4 and comprises sleeve 12' of circumferential elasticity only having an inside elastic gripping strip 18' extending around its inner circumference. A U-shaped strap 14' composed of substantially inelastic material extends rearwardly from the sleeve 12' and around the ankle (see FIG. 6). One end of the strap 14' attaches to the lateral side of the sleeve approximately adjacent the bottom of the foot, i.e. approximately at the lateral plantar. The strap 14' then extends angularly upwardly along the lateral side of the arch and directly around the ankle. The other end of strap 14' connects to the medial side of the sleeve 12' at approximately the same location as strap end 14b connects to sleeve 12' in the prior embodiment. The end of the strap is secured through a metal loop in the same location of the strap end between the medial side of the sleeve and the medial plantar provides a mechanical advantage to hold the foot from turning outwardly.

The sleeve 12' of the modification can also be applied around the leg at the ankle (see FIG. 5) so that the strap 14' extends down along the sides of the ankle and under the heel. The force of the strap stabilizes the ankle and prevents excessive inward turning (inversion) and outward turning (eversion) of the ankle.

It is understood that the connection portions of the strap to the sleeve are approximate and that modifications can be made to the various embodiments without departing from the invention.

We claim:

1. Apparatus for stabilizing the foot to control gait, comprising:

a sleeve formed from an elongated sheet of material having opposite ends that can be releasably fastened together, the opposite ends of said sheet being adjustable relative to one another upon fastening for adjusting the circumference of said sleeve, said sleeve having at least limited elasticity in the circumferential direction;

gripping means included on the inside surface of said sleeve for gripping the foot and anchoring said sleeve thereto;

an elongated strap connected at a first end to said sleeve; and means for adjustably and releasably connecting a second end of said strap to said sleeve, said sleeve being sufficiently inelastic in the lateral direction, and said strap being sufficiently inelastic in the longitudinal direction, to exert resistive forces to restrain the motions of the foot to prevent excessive pronation when said sleeve is fastened around and anchored to the foot at the mid part of the arch and when said strap is wrapped around the foot and tightened to said sleeve in a prescribed manner.

2. Apparatus as set forth in claim 1, wherein said first end of said strap is connected to said sleeve at a location corresponding approximately to the lateral plantar portion of the foot when said sleeve is in place around the arch of the foot.

3. Apparatus as set forth in claim 2, wherein said means for connecting said second end of said strap is located at the medial side of said sleeve between the side center line and the medial bottom edge of the foot when said sleeve is in place around the arch of the foot.

4. Apparatus as set forth in claim 1, wherein said sleeve is formed by a subsantially rectangular sheet having opposite ends that can be releasably fastened together.

5. Apparatus as set forth in claim 1, wherein said opposite ends of said sheet include mating portions of thistle cloth fastening material.

6. Apparatus as set forth in claim 3, wherein said strap extends from said connection at the lateral plantar toward the instep underneath the foot, across the top of the foot, around the ankle, and returns to said connecting means along the medial side of said sleeve.

7. Apparatus as set forth in claim 6, wherein said strap is folded over on itself at an oblique angle intermediate said first and second ends at a location approximately underneath the lateral malleolus, whereby said strap tends to conform to the curvature of the heel.

8. Apparatus as set forth in claim 6, and further including:

means carried by said sleeve for guiding said strap around the instep and across the top of the foot, whereby said strap is maintained in the prescribed relation to the foot.

9. A method for stabilizing the foot to control gait, comprising the steps of:

placing around the arch of the foot a sleeve that is elastic in the circumferential direction so as to resist spreading of the foot when the foot strikes the ground, while allowing the sleeve to stretch in the circumferential direction and to return the foot to its initial shape when the foot is lifted from the ground, and that is sufficiently inelastic in the lateral direction to serve as a stable base from which foot restraining forces can be applied in said lateral direction;

anchoring the sleeve to the foot by means of gripping material lining the interior surface of the sleeve;

fastening one end of an elongated strap that is sufficiently inelastic to exert foot restraining forces in the longitudinal direction to the sleeve at a location corresponding to the lateral plantar portion of the foot with the strap directed generally toward the instep and rearwardly underneath the foot;

wrapping the strap obliquely across the bottom of the foot, obliquely up and over the arch, and rearwardly across the top of the foot to support the arch joints of the foot;

further wrapping the strap around the ankle and back along the medial side of the foot to resist outward turning of the foot;

tightening the strap around the heel while the foot is in a position of slight inward turn and outward roll; and fastening the other end of the strap to the sleeve at a location corresponding approximately to the medial plantar portion of the foot with the strap tightening to restrain the foot against excessive pronation and to assist in the resupination of the foot.

10. A method as set forth in claim 9, wherein said sleeve has at least limited elasticity in the circumferential direction and is substantially inelastic in the lateral direction, and further wherein said strap is substantially inelastic in the longitudinal direction.

11. A method as set forth in claim 9 or 10, wherein said sleeve includes means for gripping the foot to anchor said sleeve thereto.

* * * * *

UNITED STATES PATENT AND TRADEMARK OFFICE
CERTIFICATE OF CORRECTION

PATENT NO. : 4,392,487
DATED : July 12, 1983
INVENTOR(S) : Allen J. Selner and Marc D. Selner It is certified that error appears in the above-identified patent and that said Letters Patent is hereby corrected as shown below:

Column 1, line 44 delete "pronationn" and insert therefor --pronation--.

Column 8, claim 9, line 44-45 delete "tightening" and insert therefor --tightened--.

Signed and Sealed this

First Day of November 1983

[SEAL]

Attest:

GERALD J. MOSSINGHOFF

Attesting Officer

Commissioner of Patents and Trademarks